(12) United States Patent
Hu

(10) Patent No.: US 12,018,014 B2
(45) Date of Patent: Jun. 25, 2024

(54) PYRROLE-SUBSTITUTED INDOLONE DERIVATIVE OR PHARMACEUTICALLY ACCEPTABLE SALTS THEREOF, AND PREPARATION METHOD THEREFOR AND APPLICATION THEREOF

(71) Applicants: SUZHOU GENHOUSE PHARMACEUTICAL CO., LTD., Jiangsu (CN); SHANDONG NEW TIME PHARMACEUTICAL CO., LTD., Shandong (CN)

(72) Inventor: Lihong Hu, Shanghai (CN)

(73) Assignees: SUZHOU GENHOUSE PHARMACEUTICAL CO., LTD., Suzhou (CN); SHANDONG NEW TIME PHARMACEUTICAL CO., LTD., Linyi (CN)

( * ) Notice: Subject to any disclaimer, the term of this patent is extended or adjusted under 35 U.S.C. 154(b) by 642 days.

(21) Appl. No.: 17/275,683

(22) PCT Filed: Sep. 19, 2018

(86) PCT No.: PCT/CN2018/106524
§ 371 (c)(1),
(2) Date: Mar. 12, 2021

(87) PCT Pub. No.: WO2020/056634
PCT Pub. Date: Mar. 26, 2020

(65) Prior Publication Data
US 2022/0098174 A1 Mar. 31, 2022

(51) Int. Cl.
*C07D 401/14* (2006.01)
*A61P 35/02* (2006.01)
*C07D 403/06* (2006.01)

(52) U.S. Cl.
CPC ............ *C07D 401/14* (2013.01); *A61P 35/02* (2018.01); *C07D 403/06* (2013.01)

(58) Field of Classification Search
CPC .................................................. C07D 401/14
See application file for complete search history.

(56) References Cited

U.S. PATENT DOCUMENTS

| | | | |
|---|---|---|---|
| 9,556,154 B2 * | 1/2017 | Hu | ........................ C07D 401/14 |
| 2016/0347740 A1 | 12/2016 | Hu et al. | |

FOREIGN PATENT DOCUMENTS

| | | |
|---|---|---|
| CN | 101007801 A | 8/2007 |
| CN | 108727341 A | 11/2018 |
| WO | 2007085205 A1 | 8/2007 |
| WO | 2012119979 A1 | 9/2012 |

OTHER PUBLICATIONS

International Search Report in PCT/CN2018/106524 dated Jun. 19, 2019, 6 pages.
Written Opinion in PCT/CN2018/106524 dated Jun. 19, 2019, 8 pages.
Wang, Jingbing et al., Synthesis of (S)-(-)-5-(p-benzyloxybenzyl)-2, 4-oxazolidinedione, Chinese Journal of Synthetic Chemistry, 17(3): 320-323, 2009.
First Office Action in Chinese Application No. 201710240681.2 dated Mar. 18, 2020, 12 pages.
Gilliland, D. G. et al., Focus on Acute Leukemias, Cancer Cell, 1: 417-420, 2002.
Marrin, C. et al., Pacritinib Suppresses Leukemic Outgrowth from FLT3-ITD Positive Stroma-Adherent Primary AML Cells, Blood, 124(21): 270, 2014.
Choudhary, C. et al., Signal Transduction of Oncogenic Flt3, International Journal of Hematology, 82: 93-99, 2005.
Paul, William Manley et al., Advances in the Structural Biology, Design and Clinical Development of VEGF-R Kinase Inhibitors for the Treatment of Angiogenesis, Biochimica et Biophysica Acta, 1697: 17-27, 2004.
Anne-Marie, O'Farrell et al., SU11248 is a Novel FLT3 Eyrosine Kinase Inhibitor with Potent Activity in Vitro and inVivo, Blood, 101(9): 3597-3605, 2003.
Anne-Marie, O'Farrell et al., An Innovative Phase I Clinical Study Demonstrates Inhibition of FLT3 Phosphorylation by SU11248 in Acute Myeloid Leukemia Patients, Clinical Cancer Research, 9(15): 5465-5476, 2003.
Fiedler, W. et al., A Phase 1 Study of SU11248 in the Treatment of Patients with Refractory or Resistant Acute Myeloid Leukemia (AML) or not Amenable to Conventional Therapy for the Disease, Blood, 105(3): 986-993, 2005.
The Extended European Search Report in European Application No. 18934491.4 dated Feb. 16, 2022, 8 pages.
Ma, Fei et al., Design, synthesis and biological evaluation of indolin-2-one-based derivatives as potent, selective and efficacious inhibitors of FMS-like tyrosine Icinase3 (FLT3), European Journal of Medicinal Chemistry, 127: 72-86, 2017.

\* cited by examiner

*Primary Examiner* — Golam M Shameem
(74) *Attorney, Agent, or Firm* — METIS IP LLC

(57) ABSTRACT

A pyrrole-substituted indolone derivative or pharmaceutically acceptable salts thereof, and a preparation method therefor and application thereof. The pyrrole-substituted indolone derivative or pharmaceutically acceptable salts thereof is simple to synthesize, easy to prepare, rich in raw materials for synthesis, and has an inhibitory effect on a plurality of tyrosine kinases, especially has higher selective inhibitory activity against KDR (VEGFR2), and FLT3 and its mutants, and can avoid toxic side effects caused by inhibiting KDR.

9 Claims, No Drawings

PYRROLE-SUBSTITUTED INDOLONE DERIVATIVE OR PHARMACEUTICALLY ACCEPTABLE SALTS THEREOF, AND PREPARATION METHOD THEREFOR AND APPLICATION THEREOF

CROSS-REFERENCE TO RELATED APPLICATIONS

This present application is a U.S. national stage under 35 U.S.C. § 371 of International Application No. PCT/CN2018/106524, filed on Sep. 19, 2018, designating the United States of America, the contents of which are incorporated herein by reference.

TECHNICAL FIELD

The present disclosure relates to the field of medicine, in particular to a pyrrole-substituted indolone derivative or pharmaceutically acceptable salts thereof, and a preparation method therefor and application thereof.

BACKGROUND

Leukemia is a type of malignant clonal disease of hematopoietic stem cells, also known as blood cancer. Acute Myeloid Leukemia (AML) is the most common acute leukemia in adults, accounting for 40% of the total incidence of leukemia and about 80% of the total incidence of acute leukemia. The cause of AML is abnormal proliferation and differentiation of immature myeloid progenitor cells resulting from abnormal differentiation of primitive hematopoietic stem cells and progenitor cells. (Gilliland, D. G. et al. Cancer Cell, 2002, 1, 417). The current treatment methods for AML mainly include drug therapy and bone marrow transplantation. Drug therapy mainly refers to traditional chemotherapy, which can be divided into two stages of induction remission treatment and post-remission treatment. At present, the induction remission treatment for AML is still based on anthracycline antitumor antibiotics combined with cytarabine. The post-remission treatment includes consolidation intensive treatment, maintenance treatment, and prevention and treatment of central nervous system leukemia, and high-dose cytarabine combined chemotherapy is generally chosen. In recent years, through the improvement of supportive treatment and the increase of chemotherapy intensity, the efficacy of chemotherapy has been improved. The total complete remission rate of chemotherapy for AML patients can reach 50% to 70%, and the long-term disease-free survival rate is 25% to 30%. However, due to the significant individual heterogeneity and high recurrence rate of AML, a considerable proportion of patients still have poor results or relapse. Hematopoietic stem cell transplantation (HSCT) is a reliable method to cure AML. Nevertheless, patients still have the risk of relapse after transplantation. The recurrence rate of standard-risk patients is 8% to 12%, and for high-risk patients the recurrence rate can reach 39% to 74%. Post-transplant recurrence is one of the main reasons for transplant failure.

Researching into and developing new AML treatment drugs to improve the effective rate of drug therapy and prolong survival is still an urgent need for AML patients. FMS-like tyrosine kinase 3 (FLT3) is a new AML therapeutic target that has attracted much attention in recent years. Studies show that FLT3 protein is mainly expressed in normal myeloid and lymphoid cell precursors, and is expressed in 70% to 90% of AML and acute lymphocytic leukemia cells. The FLT3 protein belongs to the protein tyrosine kinase (PTK) family, which was independently and separately discovered by the Rosnet research group and the Matthews research group in 1991. The FLT3 protein belongs to the protein tyrosine receptor III family, and consists of an extracellular domain containing five immunoglobulins, a transmembrane domain, a juxtamembrane fragment, and a cytoplasmic region. A large number of studies show that the mutation and abnormal activation of the tyrosine kinase FLT3 protein are closely related to the occurrence and development of AML (Marrin, C. et al. Blood, 2014, 124, 3). The first type of mutation is tandem duplication of the juxtamembrane fragment (Internal Tandem Duplication, ITD), which accounts for about 23% of the FLT3 protein mutations. The second type of mutation is point mutation of an activation domain (Tyrosine Kinase Domain, TKD), which accounts for about 8% of the mutations in the FLT3 protein. The third type of mutation is point mutation in the juxtamembrane fragment, which accounts for about 2% of the FLT3 protein mutation. After FLT3 protein mutation, it will induce FLT3 protein dimerization, which in turn leads to receptor autophosphorylation. At the same time, the activation domain in the cytoplasm comes close to the membrane, and the intracellular substrate is more easily combined with the active binding site of FLT3, resulting in the activation of FLT3. After the activation of FLT3, FLT3 activates the downstream Ras pathway and Phosphatidyl Inositol 3-Kinase (PI3K) pathway, and then regulates the apoptotic and anti-apoptotic factors in the pathways to affect cell growth, proliferation and survival to achieve the effect of inhibiting tumor growth (Choudhary, C. et al. Int. J. Hematol., 2005, 82, 93-99). In view of the role of FLT3 in the occurrence and development of AML, the FLT3 protein can be used as an important target for the treatment of AML. Therefore, the development of efficient, safe and low-toxic FLT3 inhibitors has certain scientific value and social significance for the treatment of AML.

Sunitinib is a multi-target tyrosine kinase inhibitor developed by Pfizer. It mainly inhibits PDGFR-β and VEGFR-2 in vascular endothelial cells to exert anti-neoangiogenesis effect, and can also act on tumor cells with abnormally-activated RTKs to exert a direct anti-tumor effect. Sunitinib was approved to come into the market by the FDA in 2006 for the treatment of gastrointestinal stromal tumors and renal cell carcinoma, and later was approved for the treatment of progressive pancreatic neuroendocrine tumors (pNET) that cannot be surgically removed or have spread (metastasis). Sunitinib has a strong inhibitory effect on VEGFR-1, VEGFR-2, VEGFR-3, PDGFR-s, c-Kit, FLT3 and other receptor tyrosine kinases: VEGFR-1 ($IC_{50}$: 15.1 nM), VEGFR-2 ($IC_{50}$: 38.1 nM), VEGFR-3 ($IC_{50}$: 30.6 nM), PDGFR-β ($IC_{50}$: 55.1 nM), c-Kit ($IC_{50}$: 211.34 nM), CSF-1R ($IC_{50}$: 35.6 nM), FlT3 ($IC_{50}$: 21.5 nM) (PWManley et al. Biochimica et Biophysica Acta, 2004, 1697, 17). Although FLT3 can be inhibited at the nM level, Sunitinib also has considerable inhibitory activity against neoangiogenesis-related VEGFR, PDGFR and the like. It is shown that sunitinib is a non-selective FLT3 inhibitor, and has strong inhibitory activity against FLT3-ITD and FLT3-TKD with FLT3 mutation. Sunitinib can inhibit FLT3-mediated phosphorylation in vitro, induce cell apoptosis, and inhibit in vitro proliferation of FLT3-ITD positive cell strains. Oral administration of 20 mg/kg/d showed a significant tumor inhibitory effect in MV-4-11 (FLT3-ITD) nude mouse xenograft tumor model. A single administration can maintain the FLT3-ITD phosphorylation inhibitory effect for 16 hours. (Anne-Mare O'Farrell, Tinya J. Abrams, et al. *Blood*, 2003, 101(9), 3597.)

In a phase I clinical study, 29 patients with AML who were refractory and relapsed or were not suitable for standard treatment were selected to receive a single dose of Sunitinib from 50 mg to 350 mg. Tolerability was observed, and a PK/PD correlation study is conducted. The result showed that drug-related adverse reactions were observed in 31% of the patients, mainly gastrointestinal reactions such as diarrhea and vomiting, and were limited to a dose of no less than 250 mg, with a degree of ½. A strong inhibitory effect on FLT3 phosphorylation was observed in more than 50% of the patients at a dose of no less than 200 mg, and related downstream signaling pathways were inhibited. (Anne-Mane O'F, James M. F, et al. *Clinical Cancer Research*, 2003, 9(15), 5465.)

In a phase I clinical study of sunitinib for AML by Fiedler et al., 16 patients with relapsed or refractory AML were divided into two groups A and B, and they were treated with different administrations (group A: 50 mg·d$^{-1}$, 4/2 scheme, group B: 75 mg·d$^{-1}$, 4/1 scheme). The results showed that 1 case had a morphological reaction, 5 cases had partial reaction (PR), the toxic reaction of the 50 mg group was similar to that in the clinical trials in solid tumors, but the incidence of bone marrow suppression increased, while the tolerance of the patients in the 75 mg group decreased, resulting in grade 4 dose-limiting fatigue and hypertension (Fiedler, W. et. al. *Blood*, 2005, 105, 986). It can be seen that although early clinical studies of Sunitinib showed certain therapeutic effects on AML, its toxic side effects were relatively strong, the tolerated dose was low, and the plasma exposure required for FLT3 inhibitory activity could not be achieved. Sunitinib was not successful when used as an FLT3 inhibitor in the treatment of AML. Therefore, it is necessary to optimize its chemical structure to reduce toxic side effects, optimize druggability, and find a safer and more effective ideal drug.

SUMMARY

In view of the shortcomings of the prior art mentioned above, an object of the present disclosure is to provide a pyrrole-substituted indolinone derivative or pharmaceutically acceptable salts thereof, and preparation method therefor and application thereof, for solving the problems in the prior art.

In order to achieve the above object and other related objects, a first aspect of the present disclosure provides a compound or pharmaceutically acceptable salts thereof. The structural formula of the compound is as shown in Formula I:

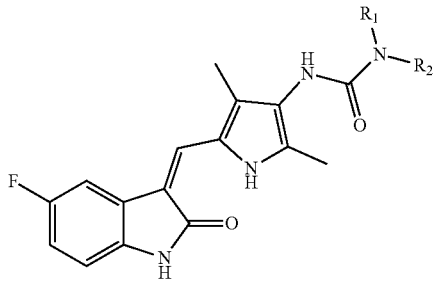

Formula I wherein, $R_1$ is selected from H; linear or branched, substituted or unsubstituted C1-C6 alkyl; $R_2$ is selected from substituted or unsubstituted heterocydoalkyl; or $R_1$ and $R_2$ form substituted or unsubstituted heterocycloalkyl with the bridged nitrogen atom.

In some embodiments of the present disclosure, $R_1$ is selected from H, linear or branched C1-C3 alkyl.

In some embodiments of the present disclosure, $R_2$ is selected from monosubstituted, polysubstituted or unsubstituted 5-membered or 6-membered heterocycloalkyl, and the substituent is selected from linear or branched C1-C3 alkyl.

In some embodiments of the present disclosure, $R_1$ and $R_2$ and the bridged nitrogen atom form monosubstituted, polysubstituted or unsubstituted 5-membered or 6-membered heterocydoalkyl, and the substituent is selected from linear or branched C1-C3 alkyl, amino.

In some embodiments of the present disclosure, the heterocycloalkyl formed by $R_1$ and $R_2$ and the bridged nitrogen atom includes one or two nitrogen atoms. Preferably, when the heterocydoalkyl includes two nitrogen atoms, it may be substituted by one or more alkyl groups, and when the heterocycloalkyl includes one nitrogen atom, it is substituted by one or more amino groups and/or aminoalkyl groups.

In some embodiments of the present disclosure, $R_1$ is selected from H, methyl, ethyl, n-propyl, isopropyl.

In some embodiments of the present disclosure, $R_2$ is selected from 4-piperidinyl and N-methyl-4-piperidinyl.

In some embodiments of the present disclosure, $R_1$ and $R_2$ form groups as shown below with the bridged nitrogen atom:

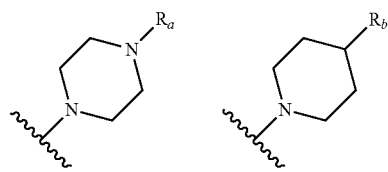

wherein, Ra is selected from linear or branched C1-C3 alkyl; Rb is selected from amino; linear or branched, substituted or unsubstituted C1-C3 alkyl, and the substituent is selected from amino.

In some embodiments of the present disclosure, the compound or pharmaceutically acceptable salts thereof is selected from a compound of Formula 1, a compound of Formula 2, a compound of Formula 3, a compound of Formula 4, a compound of Formula 5, a compound of Formula 6, a compound of Formula 7, and a compound of Formula 8.

A second aspect of the present disclosure provides a method for preparing the compound or pharmaceutically acceptable salts thereof, which comprises the following step: a compound of Formula VI reacts with a compound of Formula VII and a compound of Formula IX in the presence of an alkali, respectively, to produce the compound of Formula I. The reaction equation is as below:

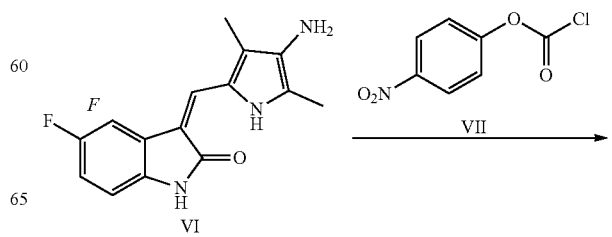

-continued

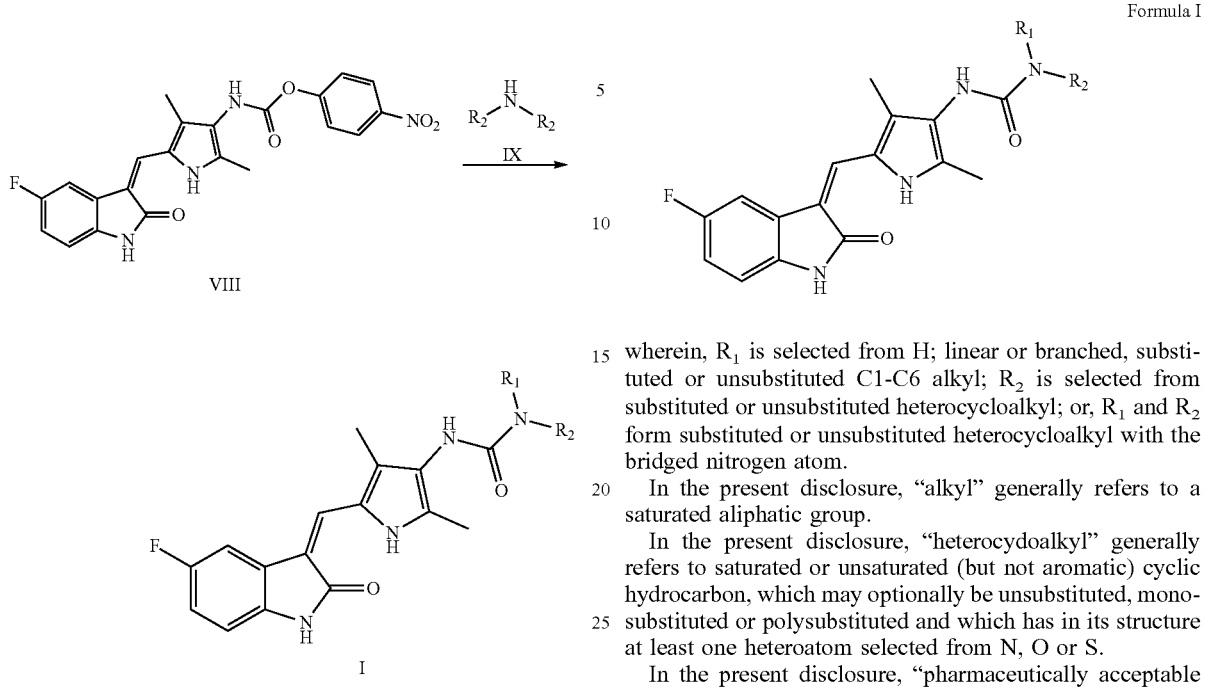

wherein, $R_1$ and/or $R_2$ in the compound of Formula IX have/has the same definition as that in the compound of Formula I.

A third aspect of the present disclosure provides the use of the compound or pharmaceutically acceptable salts thereof in the preparation of receptor tyrosine kinase inhibitors.

In some embodiments of the present disclosure, the inhibitor is a multi-target receptor tyrosine kinase inhibitor.

In some embodiments of the present disclosure, the receptor tyrosine kinase is FLT3 or mutants thereof.

In some embodiments of the present disclosure, the inhibitor is a selective inhibitor, more specifically a selective inhibitor for FLT3 or its mutants.

A fourth aspect of the present disclosure provides the use of the compound or pharmaceutically acceptable salts thereof in the preparation of a medicament for the treatment of tumors. The tumor is preferably selected from AML.

A fifth aspect of the present disclosure provides a pharmaceutical composition comprising the compound or pharmaceutically acceptable salts thereof.

DETAILED DESCRIPTION

Through a lot of practice and research, the inventor of the present disclosure provides a pyrrole-substituted indolinone derivative, which has a notable inhibitory effect on receptor tyrosine kinase (RTKs) and has the characteristics of low toxic side effects. On this basis, the present disclosure has been completed.

One aspect of the present disclosure provides a compound or pharmaceutically acceptable salts thereof. The compound is a pyrrole-substituted indolinone derivative. The structural formula of the compound is shown in Formula I:

wherein, $R_1$ is selected from H; linear or branched, substituted or unsubstituted C1-C6 alkyl; $R_2$ is selected from substituted or unsubstituted heterocycloalkyl; or, $R_1$ and $R_2$ form substituted or unsubstituted heterocycloalkyl with the bridged nitrogen atom.

In the present disclosure, "alkyl" generally refers to a saturated aliphatic group.

In the present disclosure, "heterocydoalkyl" generally refers to saturated or unsaturated (but not aromatic) cyclic hydrocarbon, which may optionally be unsubstituted, mono-substituted or polysubstituted and which has in its structure at least one heteroatom selected from N, O or S.

In the present disclosure, "pharmaceutically acceptable salts" generally refers to any salt that is physiologically tolerant (usually non-toxic) when used for treatment in an appropriate manner, especially when the object of application is human and/or mammal. More specifically, the pharmaceutically acceptable salts are usually salts formed by the compound (usually protonated) provided by the present disclosure and at least one physiologically tolerant anion. For example, the salts can be formed by hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid or the like.

In the compound of Formula I provided by the present disclosure, $R_1$ can be more specifically selected from H, linear or branched C1-C3 alkyl. In some embodiments of the present disclosure, $R_1$ is selected from H, methyl, ethyl, n-propyl, and isopropyl.

In the compound of Formula I provided by the present disclosure, $R_2$ is selected from monosubstituted, polysubstituted or unsubstituted 5-membered or 6-membered heterocydoalkyl, and the substituent may be linear or branched C1-C3 alkyl, for example, methyl, ethyl, n-propyl, or isopropyl. In some embodiments of the present disclosure, $R_2$ is selected from 4-piperidinyl and N-methyl-4-piperidinyl.

In the compound of Formula I provided by the present disclosure, $R_1$ and $R_2$ can form monosubstituted, polysubstituted or unsubstituted 5-membered or 6-membered heterocycloalkyl with the bridged nitrogen atom, and the heterocycloalkyl formed can usually include one or two nitrogen atoms. When calculating the nitrogen atoms, the bridged nitrogen atom is usually included. The substituent may be linear or branched C1-C3 alkyl, amino, etc. For example, the heterocycloalkyl formed by $R_1$ and $R_2$ and the bridged nitrogen atom may be 6-membered heterocycloalkyl, which may include two nitrogen atoms and may be substituted by one or more alkyl groups and which may also include a nitrogen atom and can be substituted by one or more amino groups. According to a specific embodiment of the present disclosure, $R_1$ and $R_2$ and the bridged nitrogen atom form a group as shown below:

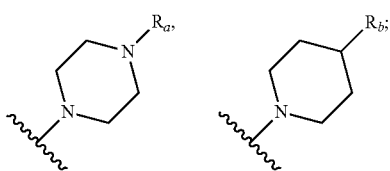

wherein, Ra is selected from linear or branched C1-C3 alkyl (for example, methyl, ethyl, n-propyl, isopropyl); and Rb is selected from amino, linear or branched C1-C3 alkyl (for example, methyl, ethyl, n-propyl, isopropyl).

The compound of Formula I or pharmaceutically acceptable salts thereof provided by the present disclosure may specifically be a compound of Formula 1, a compound of Formula 2, a compound of Formula 3, a compound of Formula 4, a compound of Formula 5, a compound of Formula 6, a compound of Formula 7, or a compound of Formula 8. The structural formulas of the compounds of Formulas 1 to 8 are shown in Table 1:

TABLE 1

| Serial Number of Compound | Structural Formula of Compound |
|---|---|
| 1 | |
| 2 | |
| 3 | |

TABLE 1-continued

| Serial Number of Compound | Structural Formula of Compound |
| --- | --- |
| 4 | 5-fluoro-3-[(3,5-dimethyl-4-{[(4-aminopiperidin-1-yl)carbonyl]amino}-1H-pyrrol-2-yl)methylene]-1,3-dihydro-2H-indol-2-one hydrochloride |
| 5 | 5-fluoro-3-[(3,5-dimethyl-4-{[(4-methylaminopiperidin-1-yl)carbonyl]amino}-1H-pyrrol-2-yl)methylene]-1,3-dihydro-2H-indol-2-one hydrochloride |
| 6 | 5-fluoro-3-[(3,5-dimethyl-4-{[(piperidin-4-yl)aminocarbonyl]amino}-1H-pyrrol-2-yl)methylene]-1,3-dihydro-2H-indol-2-one hydrochloride |
| 7 | 5-fluoro-3-[(3,5-dimethyl-4-{[(1-methylpiperidin-4-yl)aminocarbonyl]amino}-1H-pyrrol-2-yl)methylene]-1,3-dihydro-2H-indol-2-one |
| 8 | 5-fluoro-3-[(3,5-dimethyl-4-{[N-methyl-N-(piperidin-4-yl)aminocarbonyl]amino}-1H-pyrrol-2-yl)methylene]-1,3-dihydro-2H-indol-2-one hydrochloride |

Another aspect of the present disclosure provides a method for preparing the compound, which comprises the following step: a compound of Formula VI reacts with a compound of Formula VII and a compound of Formula IX respectively in the presence of an alkali to produce the compound of Formula I. The reaction equation is as below:

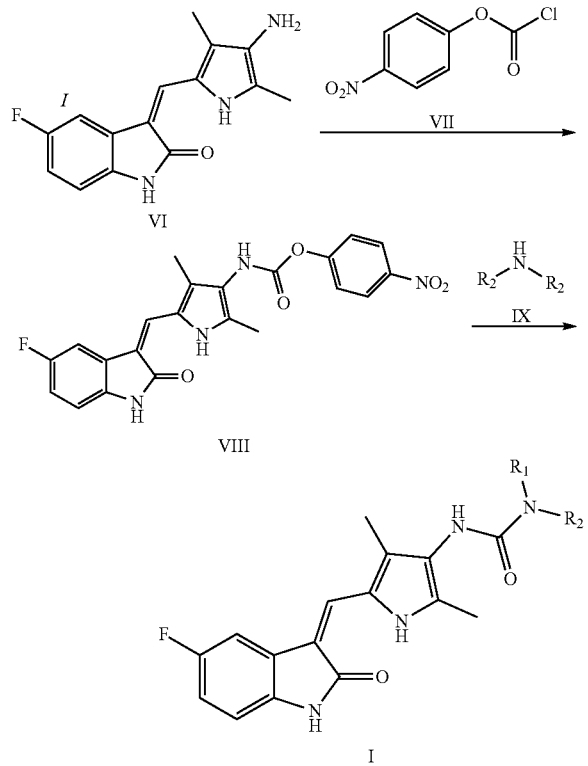

wherein, $R_1$ and/or $R_2$ in the compound of Formula IX have/has the same definition as that in the compound of Formula I.

In the above reaction, the compound of Formula VI usually reacts with the compound of Formula VII in the presence of an alkali to produce a compound of Formula VIII, and the compound of Formula VIII further reacts with the compound of Formula IX in the presence of an alkali to produce the compound of Formula I.

In the reaction of preparing the compound of Formula I from the compound of Formula VI, the amount of the compound of Formula VII and/or the compound of Formula IX used is usually equal to or greater than the amount of the compound of Formula VI used. For example, the molar ratio of the compound of Formula VII to the compound of Formula VI can be 1-1.5:1, and the molar ratio of the compound of Formula IX to the compound of Formula VI can be 1-5:1.

In the reaction of preparing the compound of Formula I from the compound of Formula VI, the alkali may usually be an organic alkali, for example, DIPEA or the like. The amount of the alkali used is usually equal to or greater than the amount of the compound of Formula VI. For example, the molar ratio of the alkali to the compound of Formula VI can be 1-1.5:1.

In the reaction of preparing the compound of Formula I from the compound of Formula VI, the reaction can be carried out in a solvent, and the solvent can usually be an aprotic solvent. Those skilled in the art can select a suitable type of the solvent and an appropriate amount of the solvent according to the raw materials in the reaction such that the raw materials have good solubility in the solvent. For example, the solvent may be tetrahydrofuran (THF) or the like.

In the reaction of preparing the compound of Formula I from the compound of formula VI, the reaction temperature can be from room temperature to the reflux temperature of the solvent; for example, the reaction can be carried out at room temperature. The reaction can usually be carried out under the condition of gas protection. The gas used to create the condition of gas protection can be nitrogen, inert gas, etc., and more specifically the inert gas can be helium, neon, argon, krypton, xenon, etc. Those skilled in the art can adjust the reaction time according to the reaction process. The reaction process can be monitored by methods such as TLC and HPLC. The reaction time can be 0.1-24 h. After the reaction is completed, the reaction product can be desolvated and purified to obtain the compound of Formula I. Those skilled in the art can choose a suitable method for purification. For example, a suitable solvent can be used to rinse the product. Further, for example, the solvent that can be used can be one of water, ethyl acetate (EA), methanol, etc. or a combination of several of them. The compound of Formula I may further form pharmaceutically acceptable salts thereof with a suitable acid.

Further, the preparation method of the compound of Formula VI may include the following step: the compound of Formula V is subjected to a reduction reaction in an electrolyte solution to produce the compound of Formula VI. The reaction equation is as below:

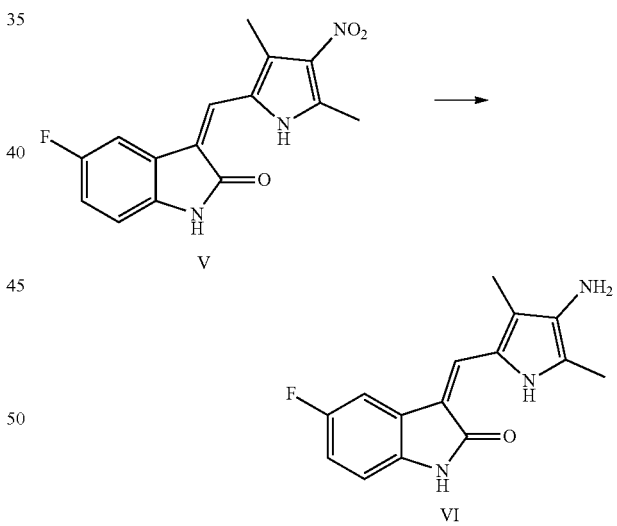

In the reaction of preparing the compound of Formula VI from the compound of Formula V, the reducing agent used in the reduction reaction normally can be, for example, one of Zn powder, Fe powder, etc. or a combination of several of them. The amount of the reducing agent used is usually equal to or greater than that of the compound of Formula V. For example, the molar ratio of the reducing agent to the compound of Formula V can be 1-50:1.

Those skilled in the art can select a suitable electrolyte solution for reducing the compound of Formula V to the compound of Formula VI. For example, the electrolyte may be one of ammonium chloride, etc. or a combination of several of them, and the concentration of the electrolyte in the solution may be 1/10 to 1/2 of its saturation concentration. Further, for example, the solvent for forming the electrolyte solution may be one of water, tetrahydrofuran, methanol, etc. or a combination of several of them. Further, for example, the concentration of the compound of Formula V in the electrolyte solution may be 1-20 mmol/L. In a specific embodiment of the present disclosure, the solvent for forming the electrolyte solution is a mixture of water, tetrahydrofuran and methanol, wherein the volume ratio of water, tetrahydrofuran and methanol is 1:0.5-3:0.5-3.

In the reaction of preparing the compound of formula VI from the compound of formula V, the reaction temperature of the reduction reaction may be from room temperature to the reflux temperature of the solvent; for example, the reaction may be carried out at about 50° C. The reaction can usually be carried out under the condition of gas protection. The gas used to create the condition of gas protection can be nitrogen, inert gas, etc., and more specifically the inert gas can be helium, neon, argon, krypton, xenon, etc. Those skilled in the art can adjust the reaction time according to the reaction process. The reaction process can be monitored by methods such as TLC and HPLC. The reaction time can be 0.5-24 h. After the reaction is completed, at least part of the organic solvent in the reaction product can be removed, pH is adjusted to alkaline, and organic solvent extraction and organic phase desolvation are performed to obtain the compound of Formula VI. The organic solvent used during extraction can be, for example, ethyl acetate.

Further, the preparation method of the compound of Formula V may include the following step: a compound of Formula III and a compound of Formula IV have a condensation reaction to produce the compound of Formula V. The reaction equation is as below:

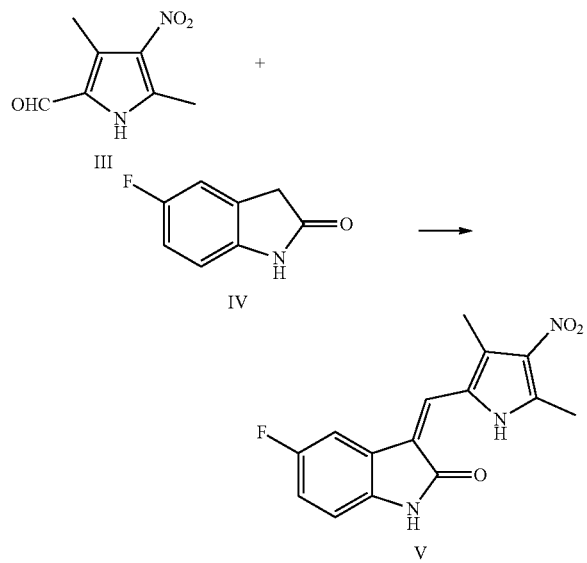

In the reaction of preparing the compound of Formula V from the compound of Formula III, the reaction is usually carried out in the presence of a catalyst. Those skilled in the art can select a suitable type and amount of the catalyst for the condensation reaction of the compound of Formula III and the compound of Formula IV. For example, the catalyst may be pyrrolidine or the like, and for example, the molar ratio of the catalyst to the compound of Formula III may be 1-1.5:1.

In the reaction of preparing the compound of Formula V from the compound of Formula III, the amount of the compound of Formula IV used is usually equal to or greater than that of the compound of Formula III. For example, the molar ratio of the compound of Formula III to the compound of Formula IV can be 1:1-1.5.

In the reaction of preparing the compound of Formula V from the compound of Formula III, the reaction can be carried out in a solvent, and the solvent usually can be a polar protic solvent. Those skilled in the art can select a suitable type and amount of the solvent according to the raw materials in the reaction such that the raw materials have good solubility in the solvent. For example, the solvent may be ethanol (EtOH) or the like.

In the reaction of preparing the compound of formula V from the compound of formula III, the reaction temperature of the reduction reaction may be from room temperature to the reflux temperature of the solvent; for example, the reaction may be carried out at about 50° C. The reaction can usually be carried out under the condition of gas protection. The gas used to create the condition of gas protection can be nitrogen, inert gas, etc., and more specifically the inert gas can be helium, neon, argon, krypton, xenon, etc. Those skilled in the art can adjust the reaction time according to the reaction process. The reaction process can be monitored by methods such as TLC and HPLC. The reaction time can be 0.5-24 h. After the reaction is completed, the reaction product can go through solid-liquid separation, and the solid phase substance is the compound of Formula V.

Further, the preparation method of the compound of Formula III may include the following step: nitrating a compound of Formula II in the presence of a nitrating agent and a dehydrating agent to produce the compound of Formula III. The reaction equation is as below:

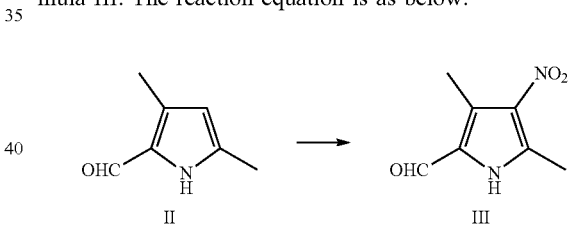

In the reaction of preparing the compound of Formula III from the compound of Formula II, those skilled in the art can select a suitable type and amount of the nitrating agent and/or dehydrating agent to carry out the nitration reaction. For example, the nitrating agent may be nitric acid, nitrate, etc., and the nitrate may be, for example, potassium nitrate, etc. The amount of the nitrating agent used generally can be equal to or greater than that of the compound of Formula II. For example, the molar ratio of the nitrating agent to the compound of Formula II may be 1-1.5:1; and the dehydration agent can be concentrated sulfuric acid and the like.

In the reaction of preparing the compound of Formula III from the compound of Formula II, the reaction temperature is usually lower than room temperature; for example, the reaction can be carried out at about −10° C. The reaction can usually be carried out under the condition of gas protection. The gas used to create the condition of gas protection can be nitrogen, inert gas, etc., and more specifically the inert gas can be helium, neon, argon, krypton, xenon, etc. Those skilled in the art can adjust the reaction time according to the reaction process. The reaction process can be monitored by methods such as TLC and HPLC. The reaction time can be 0.5-24 h. After the reaction is completed, the reaction product can be diluted with water, and go through organic solvent extraction and organic phase desolvation (after the desolvation, the reaction product can be further rinsed with an organic solvent) to obtain the compound of Formula III. The organic solvent used for extraction and/or rinse can be, for example, ethyl acetate, etc.

Another aspect of the present disclosure provides the use of the compound or pharmaceutically acceptable salts thereof in the preparation of receptor tyrosine kinase inhibitors. The compound or pharmaceutically acceptable salts thereof is specifically a multi-target receptor tyrosine kinase inhibitor, and more specifically may be an inhibitor of FLT3 or its mutants (Fms-like tyrosine kinase, FMS-like tyrosine kinase 3, For example, FLT3, FLT3-ITD, FLT3 D835Y, etc.), the FLT3 or its mutants being members of the type III receptor tyrosine kinase family. The inhibitor may be a selective inhibitor, and the selective inhibition may mean that, compared with KDR (human vascular endothelial growth factor receptor 2, VEGFR2), the compound or pharmaceutically acceptable salts thereof has a better inhibitory effect on FLT3 or its mutants. For example, compared with KDR, the compound or pharmaceutically acceptable salts thereof has an $IC_{50}$ concentration that may be no more than 10% for FLT3 or its mutants.

Another aspect of the present disclosure provides the use of the compound or pharmaceutically acceptable salts thereof in the preparation of a medicament for treating tumors. The compound or pharmaceutically acceptable salts thereof can inhibit the growth of tumor cells, and thus can be used to prepare drugs for treatment of tumors, and the tumor can be more specifically acute myelocytic leukemia (AML) and the like.

Another aspect of the present disclosure provides a pharmaceutical composition, which includes the compound or pharmaceutically acceptable salts thereof, and more specifically may include a therapeutically effective amount of the compound or pharmaceutically acceptable salts thereof. The pharmaceutical composition may also include pharmaceutically acceptable carriers, additives, adjuvants or excipients and the like.

According to the present disclosure, "therapeutically effective amount" generally refers to an amount that can achieve a therapeutic effect after a proper period of administration. Generally speaking, the reduction of one or more symptoms or clinical indicators means that the treatment is effective. A satisfactory effect means that the treatment can medically reduce one or more symptoms of the tumor or completely eliminate the tumor, or block or delay tumor occurrence and/or reduce the risk of tumor development or deterioration.

The pyrrole-substituted indolinone derivative or pharmaceutically acceptable salts thereof prepared according to the present disclosure is not only simple to synthesize, easy to prepare and rich in synthetic raw materials, but also has an inhibitory effect on a variety of tyrosine kinases, especially has a higher selective inhibitory activity against FLT3 and its mutants when compared with KDR (VEGFR2), and can avoid the toxic side effects caused by inhibiting KDR, for example, the toxic side effects related to the inhibition of extensive angiogenesis, which can increase the tolerated dose. Moreover, related experiments further show that this type of compound can selectively inhibit tumor growth, indicating that this type of compound can be used to treat a variety of tumor diseases, such as AML. In addition, the pyrrole-substituted indolinone derivative or pharmaceutically acceptable salts thereof provided according to the present disclosure has very low toxic side effects, so that such type of compound has a better application prospect.

The following describes the implementation modes of the present disclosure with reference to specific examples. Those skilled in the art can readily understand other advantages and effects of the present disclosure from the content disclosed herein. The present disclosure can also be implemented or applied through other different specific modes, and various details herein can also be modified or changed based on different viewpoints and applications without departing from the spirit of the present disclosure.

It should be noted that the process apparatuses or devices not specifically explained in the following examples are all conventional apparatuses or devices in the art.

In addition, it should be understood that the one or more steps in the methods mentioned in the present disclosure do not exclude other steps that may exist before or after the combined steps or other steps that may come between these expressly stated steps, unless otherwise specified. Furthermore, unless otherwise specified, the numbering of the respective steps only serves as a convenient tool to identify each step, not to limit the sequence of the steps or limit the scope of implementation of the present disclosure. The change or adjustment of the relative relationship between the steps, without substantial change in the technical content, should be regarded as falling within the scope of implementation of the present disclosure. All the solvents in the examples were redistilled before use, and the anhydrous solvents used were all obtained from drying treatment according to standard methods.

In each example, $^{1}$H-NMR was measured with Varian Mercury AMX300, 400, 500, and MS was measured with VG ZAB-HS or VG-7070 and Esquire 3000 plus-01005.

Unless otherwise specified, all reactions were carried out under the protection of argon and followed by TLC, and went through saturated brine rinse and anhydrous magnesium sulfate drying process during the post-treatment. Unless otherwise specified, the purification of the product used silica gel column chromatography, and the silica gel used was 200-300 mesh. $GF_{254}$ is produced by Qingdao Ocean Chemical Plant or Yantai Yuanbo Silica Gel Company.

Example 1

Preparation of the Compound of Formula 1:
Preparation of the Compound of Formula III:

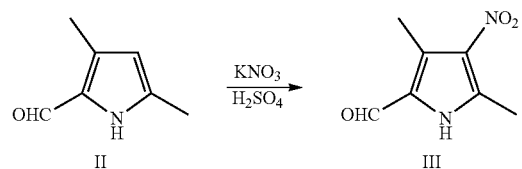

60 mL of concentrated sulfuric acid was put in a round-bottom flask with a volume of 250 mL, and a raw material of 3,5-dimethyl-2-pyrrolecarbaldehyde (compound of Formula II, 5 g, 40 mmol) was slowly added. The system was kept below −10° C. during the adding process. After the adding process, potassium nitrate (4.35 g, 42 mmol) was slowly added in batches at this temperature, and this adding process was completed in about 2 hours. In this process, the temperature was kept at −10° C., and stirring was performed at this temperature for about 2 hours after the adding process. After TLC detects completion of the reaction, the solution was added to 1 L of ice water, and was extracted twice with 1 L of ethyl acetate, and the organic layer was rinsed with saturated brine, dried with anhydrous sodium sulfate and filtered, and the organic solvent was evaporated to dryness under reduced pressure to obtain 7 g of crude product, which was added to 10-20 mL of ethyl acetate, stirred vigorously and filtered to obtain 5 g of pure target compound III. $^1$H NMR (400 MHz, Chloroform-d) δ: 10.22 (brs, 1H), 9.68 (s, 1H), 2.71 (s, 3H), 2.66 (s, 3H).

Preparation of the compound of Formula V:

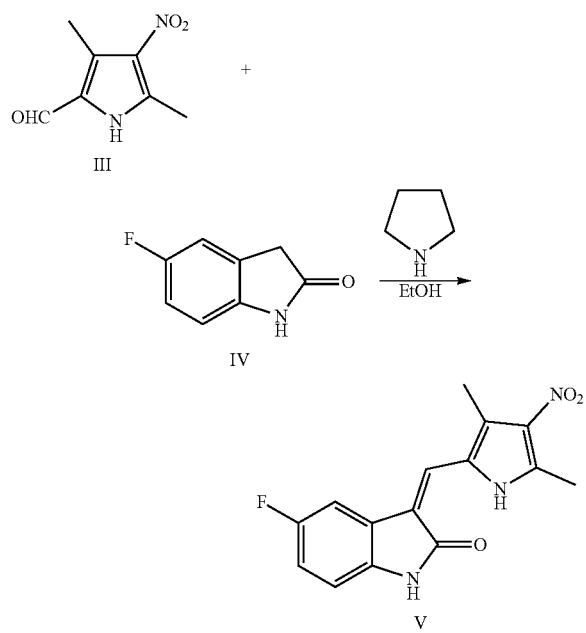

The compound III (1.68 g, 10 mmol) and the compound IV (1.8 g, 12 mmol) were added into 50 mL of absolute ethyl alcohol, and tetrahydropyrrole (850 mg, 12 mmol) was added at room temperature. After the addition, the color of the system turned yellow, the temperature was raised to 50° C., and the reaction continued for 2 hours at this temperature. After completion of the reaction, the system was directly filtered, and the filter cake was rinsed with a small amount of ethanol and ethyl acetate to obtain 2.7 g of pure target compound V. $^1$H NMR (400 MHz, DMSO-d$_6$): 11.14 (s, 1H), 7.88 (dd, J=9.2, 2.4 Hz, 1H), 7.82 (s, 1H), 7.05-6.97 (m, 1H), 6.88 (dd, J=8.5, 4.5 Hz, 1H), 2.64 (s, 3H), 2.58 (s, 3H).

Preparation of the compound of Formula VI:

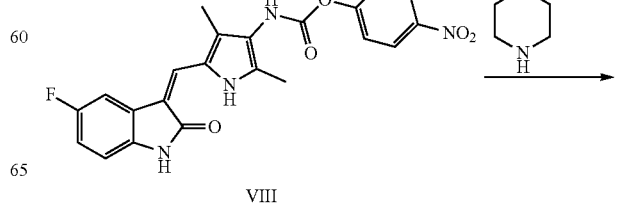

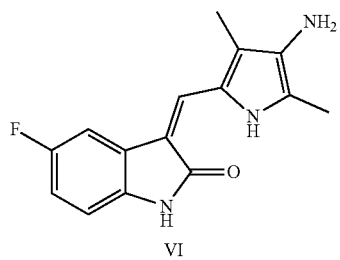

The compound V (900 mg, 3 mmol) was put into a two-necked bottle with a volume of 500 mL, and then 200 mL of tetrahydrofuran, 100 mL of methanol, 60 mL of water and 60 mL of saturated ammonium chloride solution were added into it, respectively. After the addition, the temperature was raised to 50° C., then zinc powder (1.8 g, 30 mmol) was added while stirring, and then the reaction continued for 2 hours under this condition, during which the system became clear and then turbid again. After the system became turbid, the LC-MS detected completion of the reaction. After the reaction was completed, the solution was evaporated to dryness and was added with saturated sodium carbonate solution to adjust the system to alkaline and extracted twice by 2 L of ethyl acetate. The ethyl acetate layer was rinsed with saturated brine, dried with anhydrous sodium sulfate and filtered, and the organic solvent was evaporated to dryness under reduced pressure to obtain the target compound VI (800 mg). $^1$H NMR (400 MHz, DMSO-d$_6$) δ 13.55 (s, 1H), 10.62 (s, 1H), 7.63-7.55 (m, 1H), 7.47 (s, 1H), 6.82-6.79 (m, 1H), 6.79 (d, J=1.2 Hz, 1H), 4.01 (s, 2H), 2.25 (s, 3H), 2.15 (s, 3H).

Preparation of the compound of Formula 1-A:

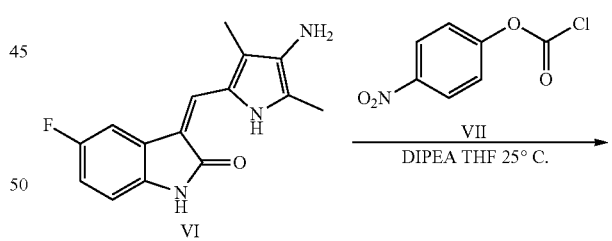

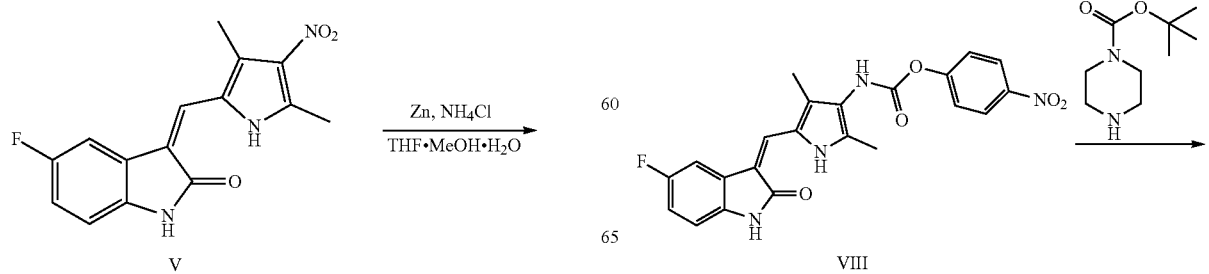

-continued

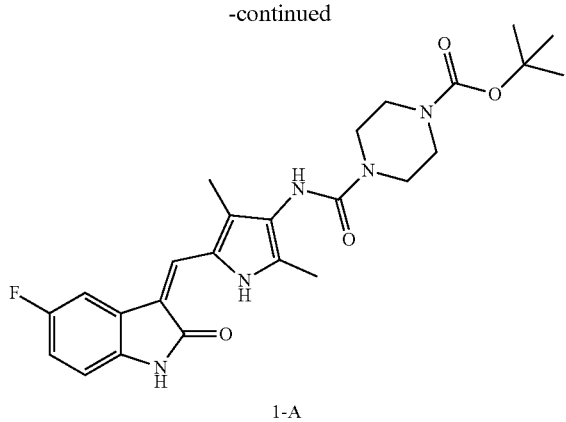

1-A

The compound VI (100 mg, 0.37 mmol) was dissolved in tetrahydrofuran (5 mL), DIPEA (0.1 mL, 0.55 mmol) was added at room temperature, and then p-nitrophenyl chloroformate (110 mg, 0.55 mmol) was added. After the addition, the reaction was carried out at room temperature for about 20 minutes, and the TLC detected completion of the reaction. After the reaction was completed, N—BOC-piperazine (275 mg, 1.48 mmol) was added to the system, and stirred for 30 minutes. The LC-MS detected completion of the reaction. After the reaction was completed, the solvent was evaporated to dryness, beaten with EA, filtered and rinsed with methanol to obtain the pure product. $^1$H NMR (400 MHz, DMSO-d$_6$) δ:13.55 (s, 1H), 10.78 (s, 1H), 7.68 (dd, J=9.5, 2.2 Hz, 1H), 7.64 (s, 1H), 7.40 (s, 1H), 6.87 (ddd, J=9.5, 9.1, 2.2 Hz, 1H), 6.82 (dd, J=8.4, 4.7 Hz, 1H), 3.37-3.20 (m, 4H), 2.20 (s, 3H), 2.17 (s, 3H), 1.82-1.88 (m, 4H).

Preparation of the compound of Formula 1:

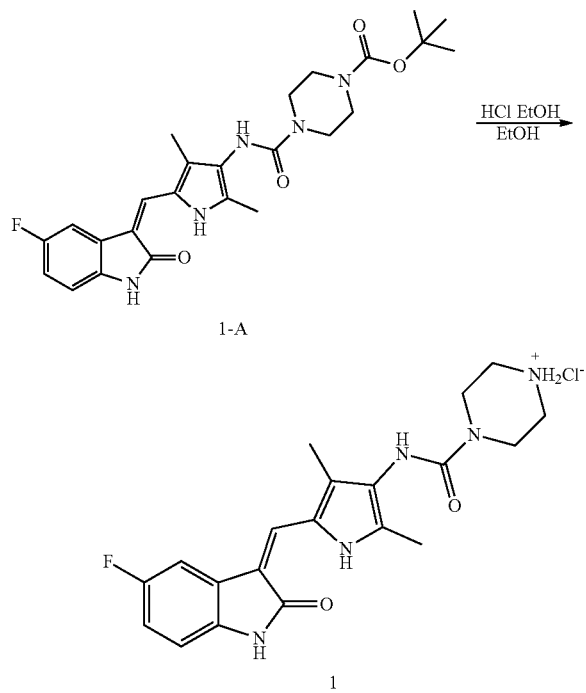

The compound of Formula 1-A (100 mg, 0.21 mmol) was dissolved in 3 mL of ethanol, then 3 mL of hydrochloric acid ethanol solution was added, and stirred for 30 minutes. The LC-MS detected completion of the reaction, and the mixture was directly spin dried to obtain the pure compound of Formula 1. $^1$H NMR (400 MHz, DMSO-d$_6$) δ:13.57 (s, 1H), 10.81 (s, 1H), 9.35 (s, 2H), 8.07 (s, 1H), 7.68 (dd, J=9.5, 2.5 Hz, 1H), 7.65 (s, 1H), 6.88 (ddd, J=9.5, 9.0, 2.5 Hz, 1H), 6.83 (dd, J=8.4, 4.7 Hz, 1H), 3.68 (t, J=5.2 Hz, 4H), 3.11 (t, J=5.2 Hz, 4H), 2.20 (s, 3H), 2.17 (s, 3H).

Example 2

Preparation of the Compound of Formula 2:

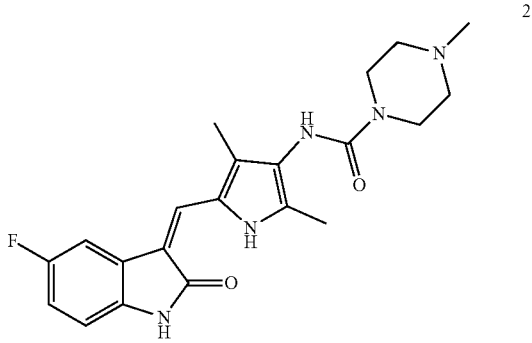

The preparation method referred to the synthesis of the compound of Formula 1, wherein N—BOC-piperazine was substituted with N-methylpiperazine to obtain the target compound of Formula 2. $^1$H NMR (400 MHz, DMSO-d$_6$) δ:13.56 (s, 1H), 10.78 (s, 1H), 7.77 (s, 1H), 7.68 (dd, J=9.5, 2.3 Hz, 1H), 7.65 (s, 1H), 6.88 (ddd, J=9.5, 9.1, 2.3 Hz, 1H), 6.83 (dd, J=8.3, 4.7 Hz, 1H), 3.45-3.39 (m, 4H), 2.33-2.28 (m, 4H), 2.20 (s, 3H), 2.19 (s, 3H), 2.16 (s, 3H).

Example 3

Preparation of the Compound of Formula 3:

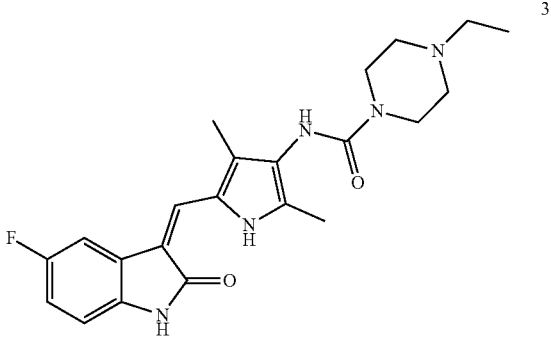

The preparation method referred to the synthesis of the compound of Formula 1, wherein N—BOC-piperazine was substituted with N-ethylpiperazine to obtain the target compound of Formula 3. $^1$H NMR (400 MHz, DMSO-d$_6$) δ:13.56 (s, 1H), 10.79 (s, 1H), 7.76 (s, 1H), 7.68 (dd, J=9.5, 2.4 Hz, 1H), 7.64 (s, 1H), 6.88 (ddd, J=9.5, 9.0, 2.5 Hz, 1H), 6.82 (dd, J=8.4, 4.7 Hz, 1H), 3.46-3.38 (m, 4H), 2.40-2.30 (m, 6H), 2.18 (s, 3H), 2.15 (s, 3H), 1.02 (t, J=7.2 Hz, 3H).

Example 4

Preparation of the Compound of Formula 4:

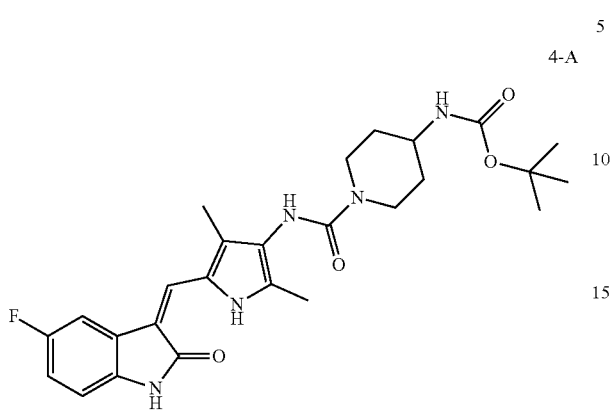

The preparation method referred to the synthesis of the compound of Formula 1, wherein N—BOC-piperazine was substituted with 4-BOC-aminopiperidine to obtain the target compound of Formula 4-A, and then BOC was removed by hydrochloric acid ethanol solution to obtain the compound of Formula 4. $^1$H NMR (400 MHz, DMSO-d$_6$) δ:13.56 (s, 1H), 10.81 (s, 1H), 8.16 (brs, 3H), 7.88 (s, 1H), 7.68 (dd, J=9.5, 2.3 Hz, 1H), 7.65 (s, 1H), 6.88 (ddd, J=9.5, 9.0, 2.3 Hz, 1H), 6.83 (dd, J=8.4, 4.8 Hz, 1H), 4.15-4.06 (m, 2H), 3.28-3.16 (m, 1H), 2.90-2.80 (m, 2H), 2.19 (s, 3H), 2.16 (s, 3H), 1.95-1.86 (m, 2H), 1.53-1.40 (m, 2H).

Example 5

Preparation of the Compound of Formula 5

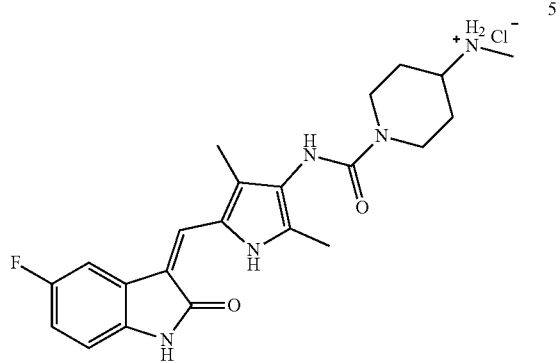

The preparation method referred to the synthesis of the compound of Formula 1, wherein N—BOC-piperazine was substituted with 4-N—BOC-4-N-methylaminopiperidine to obtain the target compound of Formula 5-A, and then BOC was removed by hydrochloric acid ethanol solution to obtain the compound of Formular 5. $^1$H NMR (400 MHz, DMSO-d$_6$) δ:13.57 (s, 1H), 10.80 (s, 1H), 8.87 (brs, 2H), 7.89 (s, 1H), 7.68 (dd, J=9.5, 2.4 Hz, 1H), 7.65 (s, 1H), 6.88 (ddd, J=9.5, 9.0, 2.4 Hz, 1H), 6.83 (dd, J=8.4, 4.8 Hz, 1H), 4.20-4.10 (m, 2H), 3.22-3.11 (m, 1H), 2.86-2.77 (m, 2H), 2.56 (s, 3H), 2.19 (s, 3H), 2.16 (s, 3H), 2.05-1.97 (m, 2H), 1.53-1.39 (m, 2H).

Example 6

Preparation of the Compound of Formula 6:

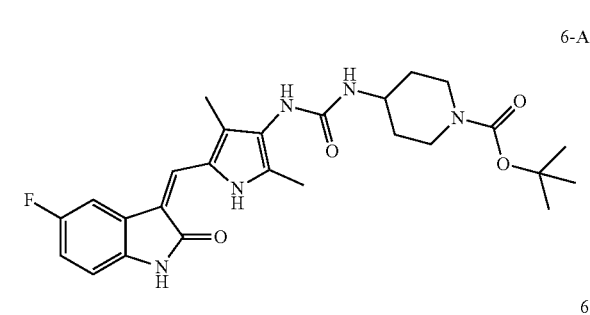

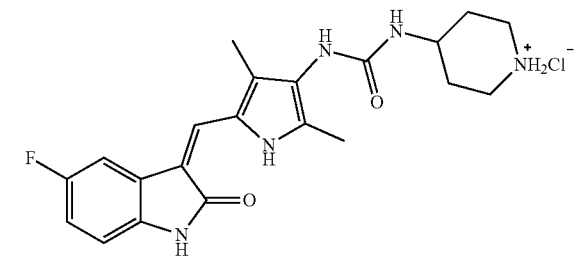

The preparation method referred to the synthesis of the compound of Formula 1, wherein N—BOC-piperazine was substituted with 1-BOC-4-aminopiperidine to obtain the target compound of Formula 6-A, and then BOC was removed by hydrochloric acid ethanol solution to obtain the compound of Formula 6. $^1$H NMR (400 MHz, DMSO-d$_6$) δ:13.56 (s, 1H), 10.80 (s, 1H), 8.78 (brs, 1H), 8.69 (brs, 1H), 7.68 (dd, J=9.5, 2.4 Hz, 1H), 7.64 (s, 1H), 7.43 (s, 1H), 6.88 (ddd, J=9.5, 9.0, 2.4 Hz, 1H), 6.83 (dd, J=8.4, 4.7 Hz, 1H), 6.49 (brs, 1H), 3.78-3.65 (m, 1H), 3.28-3.18 (m, 2H), 3.02-2.90 (m, 2H), 2.20 (s, 3H), 2.17 (s, 3H), 2.00-1.84 (m, 2H), 1.69-1.51 (m, 2H).

Example 7

Preparation of the Compound of Formula 7:

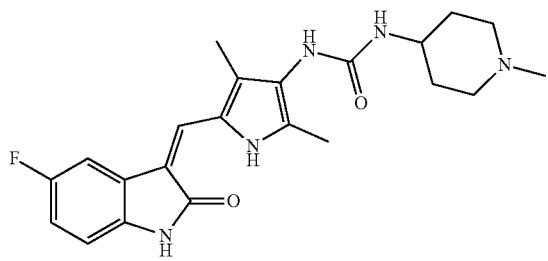

The preparation method referred to the synthesis of the compound of Formula 1, wherein N—BOC-piperazine was substituted with 1-amino-4-methylpiperazine to obtain the target compound of Formula 7. $^1$H NMR (400 MHz, DMSO-$d_6$) δ:13.55 (s, 1H), 10.79 (s, 1H), 7.68 (dd, J=9.5, 2.4 Hz, 1H), 7.63 (s, 1H), 7.28 (s, 1H), 6.87 (ddd, J=9.4, 9.0, 2.5 Hz, 1H), 6.82 (dd, J=8.4, 4.7 Hz, 1H), 5.96 (d, J=7.4 Hz, 1H), 3.45-3.36 (m, 1H), 2.65 (d, J=11.4 Hz, 2H), 2.19 (s, 3H), 2.16 (s, 3H), 2.13 (s, 3H), 1.94 (t, J=10.6 Hz, 2H), 1.76-1.69 (m, 2H), 1.45-1.32 (m, 2H).

Example 8

Preparation of the Compound of Formula 8:

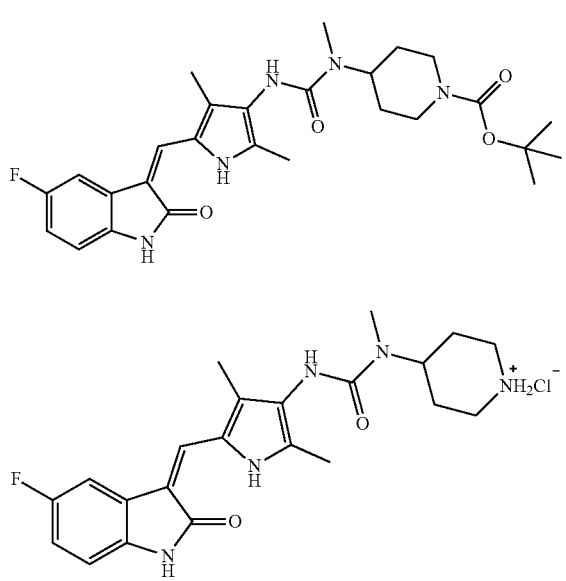

The preparation method referred to the synthesis of the compound of Formula 1, wherein N—BOC-piperazine was substituted with 1-BOC-4-methylaminopiperidine to obtain the target compound of Formula 8-A, and then BOC was removed by hydrochloric acid ethanol solution to obtain the compound of Formula 8. $^1$H NMR (400 MHz, DMSO-$d_6$) δ:13.56 (s, 1H), 10.80 (s, 1H), 8.83 (brs, 2H), 7.70-7.63 (m, 3H), 6.88 (td, J=9.5, 9.0, 2.4 Hz, 1H), 6.83 (dd, J=8.4, 4.8 Hz, 1H), 4.37-4.22 (m, 1H), 3.32-3.28 (m, 2H), 3.02-2.90 (t, J=12.6 Hz, 2H), 2.82 (s, 3H), 2.19 (s, 3H), 2.16 (s, 3H), 2.04-1.88 (m, 2H), 1.76-1.66 (m, 2H).

Example 9

Preparation of Hydrochloride of Compound of Formula 2:

0.5 mL of saturated ethanol hydrogen chloride solution was diluted ten times with absolute ethanol, the compound of Formula 2 (397 mg, 1 mmol) was added, and stirred for 5-10 minutes, and the reaction solution was concentrated under reduced pressure and rinsed with a small amount of methanol to obtain hydrochloride of the compound of Formula 2.

Hydrochlorides of all other compounds can be prepared by the corresponding compounds reacting with dilute hydrochloric acid ethanol solution by this method.

Example 10

Determination of In Vitro Biochemical Activity of Tyrosine Kinase;

The in vitro inhibitory activity of the compounds on tyrosine kinase was measured by HTRF (Homogeneous Time-Resolved Fluorescence) method.

The compounds were serially diluted with DMSO in a 96-well plate into 8 solutions of different concentrations with 100 times the final concentration. Then a buffer solution, which was prepared by adding 5 mM $MgCl_2$ and 1 mM DTT to 1-fold Enzymetic buffer provided by the kit, was diluted in a 96-well plate into a solution with 5 times the final concentration.

The diluted compounds were added to a 384-well plate, respectively, and double wells were provided for each concentration. Then 0.25 ng of kinase was added per well. At the same time, negative and positive wells were provided, and the well to which 5% DMSO of the same volume was added was taken as control. The final concentration of DMSO was 1%, and the negative well did not contain kinase. Preincubation was carried out for 10 minutes at room temperature. A substrate with a final concentration of 1 μM and ATP with a final concentration of 120 μM were added, and incubated at room temperature for 90 minutes. Then, a fluorescent acceptor (XL665 labeled streptavidin) with a final concentration of 0.0625 μM and 1-fold fluorescent donor (Europium cryptate labeled TK antibody) with a final concentration of 0.0625 μM were added, and incubated at room temperature for 60 minutes. The plates were read by a microplate reader under the conditions of λex=330 nm, λem=620 nm and λem=665 nm. A ratio between the reading at 665 nm and the reading at 620 nm was calculated, and the inhibition rate was calculated according to this ratio.

The results showed that the above-mentioned compounds of the examples (compounds of Formulas 1-8) all had significant inhibitory activity against FLT3, with $IC_{50}<20$ nM. Although they had certain inhibitory activity against KDR (VEGFR2), the inhibitory activity was relatively weak ($IC_{50}>200$ nM), showing selective FLT3 inhibitory activity. The compound of Formula 5 exhibited strong inhibitory activity against FLT3, FLT3-ITD, FLT3 D835Y, and certain inhibitory activity against PDGFRβ, c-Kit, RET, KDR, AXL, etc., with $IC_{50}>100$ nM, indicating that it was a selective FLT3 inhibitor.

TABLE 1

Inhibitory activity of the compounds of Formula 5 against various tyrosine kinases

| tyrosine kinases | IC$_{50}$ (nM) |
|---|---|
| FLT3 | 8.8 |
| FLT3-ITD | <1.5 |
| FLT3 D835Y | 17.3 |
| PDGFRβ | 189.7 |
| KDR | 891.3 |
| c-Kit | 286.4 |
| ALK | 4897.8 |
| RET | 109.9 |
| FGFR1 | 2338.8 |
| AXL | 284.5 |

Example 11

The human acute leukemia cell MV-4-11 is an Flt-3 mutant cell strain. The MTS method was used to determine the in vitro antiproliferative activity of the compound against MV-4-11 (derived from ATCC): trypsinizing the cells in the logarithmic growth phase, counting them, resuspending an appropriate number of the cells in the culture solution, adding the culture solution to the 96-well plate by 150 μL per well, and culturing it overnight. After that, 50 μL of 4-fold serially diluted test compound or control culture solution was added to each well, and cultured for 72 hours. The culture solution was drained, and 120 μL of MTS detection solution (100 μL of fresh culture medium and 20 μL of MTS solution) was added to each well, and incubated at 37° C., and the OD490 value was read. Graphpad Prism5 software was used to analyze and process the data to obtain IC$_{50}$.

The results showed that the compounds 1-8 in the above examples all exhibited significant anti proliferative activity against MV-4-11, and some compounds had the same or stronger activity as Sunitinib (see Table 2).

TABLE 2

Inhibitory effect of the compounds of Formulas 1-8 on in vitro proliferation of human MV-4-11 cell strain

| Compounds | IC$_{50}$ (nM) |
|---|---|
| 1 | 59.3 |
| 2 | 178.1 |
| 3 | 138.0 |
| 4 | 62.2 |
| 5 | 66.0 |
| 6 | 103.0 |
| 7 | 82.2 |
| 8 | 82.3 |
| Sunitinib | 74.3 |

Example 12

Inhibitory Effect on MV-4-11 Subcutaneously Transplanted Tumor in Nude Mice In Vivo;

MV-4-11 cells (FLT3-ITD mutant human acute biphenotypic myeloid leukemia cell strain, ATCC) were cultured and expanded in vitro, and the cells in the logarithmic growth phase were collected and resuspended in a serum-free EMEM culture solution, and the cell suspension was injected subcutaneously with a syringe into the armpit of the front right limb of male Balb/c nude mice. The growth of the animals and the transplanted tumor was observed on a regular basis; when the volume of the tumor grew to about 100-300 mm³, animals with moderate tumor size were randomly divided into different groups, each group consisting of 6 animals, and were given blank solvent (0.5% CMC) or the compound of Formula 5 in the above examples (the compound was hydrochloride, with doses of 2.5 mg/kg, 5 mg/kg, 10 mg/kg, 80 mg/kg, 160 mg/kg), the compound of Formula 1 in the above examples (hydrochloride, with doses of 5 mg/kg, 160 mg/kg) or Sunitinib (with doses of 10 mg/kg, 80 mg/kg), respectively, intragastric administration, once a day, and a successive administration cycle of 3 weeks; and during the administration period, the tumor diameter and the animal's weight were monitored, and the animal's living state was observed; and the experiment was terminated after 3 weeks of administration, and the animals were put to death by CO$_2$ and dissected.

The formula of calculating the tumor volume (TV) is TV=½×a×b², where a represents the long diameter of the tumor and b represents the short diameter of the tumor.

The results showed that after intragastric administration for 21 days (the 36th day after inoculation), the tumor in the solvent control group increased to nearly 6.6 times the initial volume, and the compound of Formula 5 exhibited a significant anti-tumor effect. With a dose of 2.5 mg/kg, the compound of Formula 5 showed notable inhibition on the growth of the transplanted tumor, and with a dose of no less than 5 mg/kg the transplanted tumor subsided. The anti-tumor effect at a dose of 10 mg/kg was obviously stronger than that of Sunitinib at the same dose, and was equivalent to that of Sunitinib at a dose of 80 mg/kg. Moreover, even at a dose of 160 mg/kg, the compound of Formula 5 did not show obvious toxicity to animals (nothing abnormal was detected in general clinical symptoms and anatomy, and the animal's weight was only slightly decreased). Both doses of the compound of Formula 1 made the transplanted tumors of the nude mice nearly disappear completely, and there was no obvious change in animal's weight. However, with Sunitinib at the dose of 80 mg/kg, the animal's weight decreased significantly, and toxicity was obvious, which was dose to the maximum tolerated dose.

TABLE 2

Inhibitory effect of the hydrochloride of the compound of Formula 5 on MV-4-11 transplanted tumor in nude mice

| | Dose (mg/kg) | N (start/end) | Average volume of tumor (mm³) | |
|---|---|---|---|---|
| | | | d15 | d36 |
| Solvent control | — | 6/6 | 167.59 ± 13.50 | 1118.58 ± 76.62 |
| Sunitinib | 10 | 6/6 | 167.64 ± 12.88 | 178.93 ± 13.89** |
| | 80 | 6/6 | 167.62 ± 13.27 | 22.17 ± 1.95** |
| Compound of Formula 5 | 2.5 | 6/6 | 167.76 ± 11.65 | 359.18 ± 49.62** |
| | 5 | 6/6 | 167.69 ± 11.70 | 34.71 ± 4.32** |
| | 10 | 6/6 | 167.75 ± 11.59 | 28.41 ± 3.38** |
| | 80 | 6/6 | 167.79 ± 13.04 | 19.60 ± 4.21** |
| | 160 | 6/6 | 167.59 ± 11.93 | 20.74 ± 1.38** |
| Compound of Formula 1 | 5 | 6/6 | 167.89 ± 15.27 | 18.60 ± 5.46** |
| | 160 | 6/6 | 167.70 ± 12.15 | 21.60 ± 8.29** |

Date in Table 2: Mean tumor volume (mm³) ± S.E,
n = 6
**P < 0.01, compared with the solvent control group From the experimental results of MV-4-11 transplanted tumors in nude mice, it can be found that the compound of Formula 5 (hydrochloride) and the compound of Formula 1 (hydrochloride) according to the present disclosure have a selective anti-tumor effect on human AML cells (MV-4-11) with FLT3-ITD mutation subcutaneously transplanted into nude mice. Compared with Sunitinib, the compound of Formula 5 (hydrochloride) and the compound of Formula 1 (hydrochloride) have a smaller effective dose, lower toxicity, a larger therapeutic window, and have better development value.

In summary, the present disclosure effectively overcomes various shortcomings in the prior art and has high industrial value.

It is understood that the examples described herein are only intended to explain the principles and effects of the present disclosure, instead of limiting the present disclosure. Anyone familiar with this technology can modify or change the above examples without departing from the spirit and scope of the present disclosure. Therefore, all equivalent modifications or changes made by those with general knowledge in the art without departing from the spirit and technical ideas disclosed by the present disclosure should still be covered by the protection scope of the claims of the present disclosure.

I claim:

1. A compound or pharmaceutically acceptable salts thereof, a structural formula of the compound being shown in Formula I:

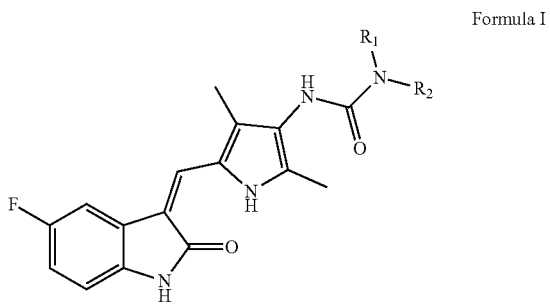

Formula I wherein,
$R_1$ is selected from H; linear or branched, substituted or unsubstituted C1-C6 alkyl;
$R_2$ is selected from substituted or unsubstituted heterocycloalkyl;
or, $R_1$ and $R_2$ form substituted or unsubstituted heterocycloalkyl with a bridged nitrogen atom.

2. The compound or pharmaceutically acceptable salts thereof according to claim 1, wherein $R_1$ is selected from H; linear or branched C1-C3 alkyl;
$R_2$ is selected from monosubstituted, polysubstituted or unsubstituted 5-membered or 6-membered heterocycloalkyl, and a substituent is selected from linear or branched C1-C3 alkyl;
or $R_1$ and $R_2$ form monosubstituted, polysubstituted or unsubstituted 5-membered or 6-membered heterocycloalkyl with a bridged nitrogen atom, and a substituent is selected from linear or branched C1-C3 alkyl, amino.

3. The compound or pharmaceutically acceptable salts thereof according to claim 1, wherein the heterocycloalkyl formed by $R_1$ and $R_2$ with the bridged nitrogen atom comprises one or two nitrogen atoms, and the heterocycloalkyl is replaceable by one or more alkyl groups when the heterocycloalkyl comprises two nitrogen atoms, and the heterocycloalkyl is replaced by one or more amino groups and/or aminoalkyl groups when the heterocycloalkyl comprises one nitrogen atom.

4. The compound or pharmaceutically acceptable salts thereof according to claim 1, wherein $R_1$ is selected from H, methyl, ethyl, n-propyl, isopropyl,
$R_2$ is selected from 4-piperidinyl and N-methyl-4-piperidinyl,
or, $R_1$ and $R_2$ form groups as shown below with a bridged nitrogen atom:

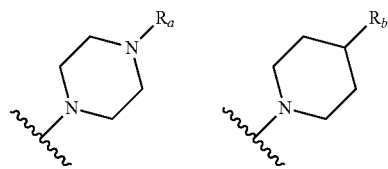

wherein, Ra is selected from linear or branched C1-C3 alkyl; Rb is selected from amino; linear or branched, substituted or unsubstituted C1-C3 alkyl, and a substituent is selected from amino.

5. The compound or pharmaceutically acceptable salts thereof according to claim 1, wherein the compound or pharmaceutically acceptable salts thereof is selected from a compound of Formula 1, a compound of Formula 2, a compound of Formula 3, a compound of Formula 4, a compound of Formula 5, a compound of Formula 6, a compound of Formula 7, and a compound of Formula 8, the structural formulas of the compounds being shown as below:

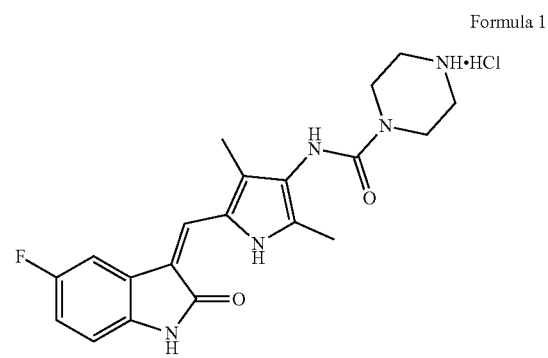

Formula 1

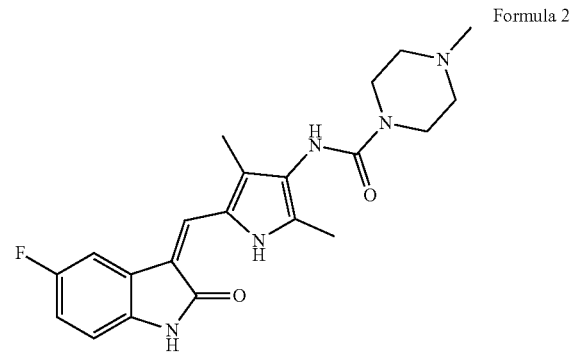

Formula 2

Formula 3
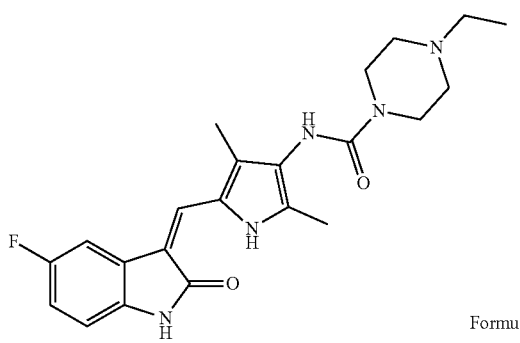

Formula 4
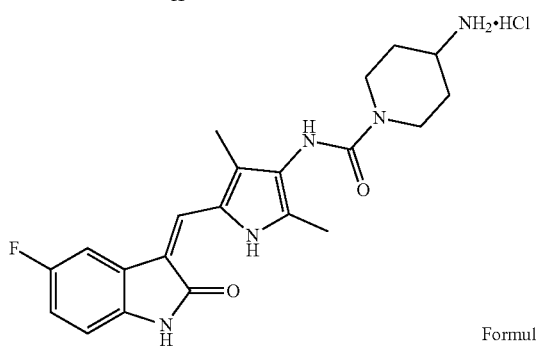

Formula 5
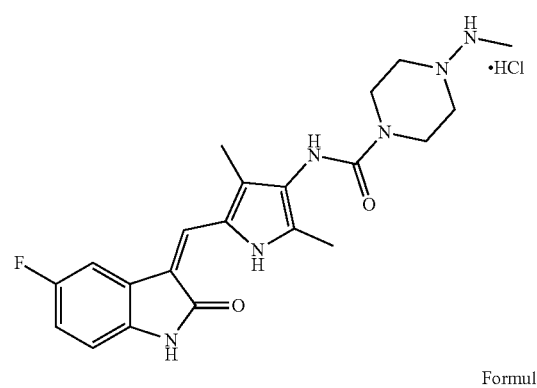

Formula 6
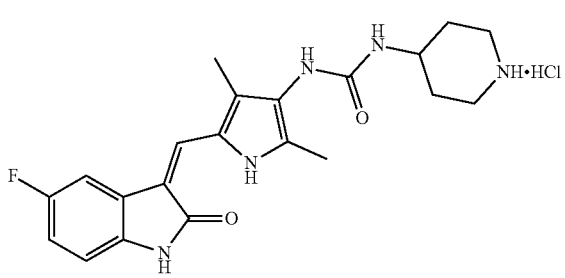

Formula 7
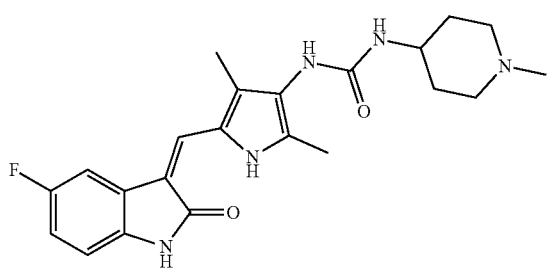 [SMILES: Cc1[nH]c(/C=C2\C(=O)Nc3ccc(F)cc32)c(C)c1NC(=O)NC1CCN(C)CC1]

Formula 8
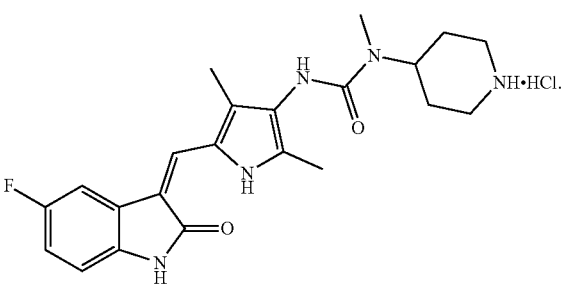

6. The compound or pharmaceutically acceptable salts thereof according to claim 1, wherein $R_1$ is selected from H, methyl, ethyl, n-propyl, isopropyl.

7. The compound or pharmaceutically acceptable salts thereof according to claim 1, wherein $R_2$ is selected from monosubstituted, polysubstituted or unsubstituted 5-membered or 6-membered heterocycloalkyl, and a substituent is selected from linear or branched C1-C3 alkyl.

8. The compound or pharmaceutically acceptable salts thereof according to claim 1, wherein $R_2$ is selected from 4-piperidinyl and N-methyl-4-piperidinyl.

9. The compound or pharmaceutically acceptable salts thereof according to claim 1, wherein $R_1$ and $R_2$ form monosubstituted, polysubstituted or unsubstituted 5-membered or 6-membered heterocycloalkyl with the bridged nitrogen atom, and the substituent is selected from linear or branched C1-C3 alkyl and amino.

* * * * *